(12) United States Patent
Lockerbie et al.

(10) Patent No.: US 7,901,673 B2
(45) Date of Patent: *Mar. 8, 2011

(54) INDUCTION OF AND MAINTENANCE OF NUCLEIC ACID DAMAGE IN PATHOGENS USING RIBOFLAVIN AND LIGHT

(75) Inventors: Robert Owen Lockerbie, Littleton, CO (US); Vijay Kumar, Westminster, CO (US); Shawn D. Keil, Wheat Ridge, CO (US); Raymond P. Goodrich, Lakewood, CO (US)

(73) Assignee: CaridianBCT Biotechnologies, LLC, Lakewood, CO (US)

(*) Notice: Subject to any disclaimer, the term of this patent is extended or adjusted under 35 U.S.C. 154(b) by 1549 days.

This patent is subject to a terminal disclaimer.

(21) Appl. No.: 10/648,536

(22) Filed: Aug. 25, 2003

(65) Prior Publication Data

US 2004/0081956 A1    Apr. 29, 2004

Related U.S. Application Data

(63) Continuation of application No. 10/377,524, filed on Feb. 28, 2003, which is a continuation of application No. 09/586,147, filed on Jun. 2, 2000, now abandoned.

(60) Provisional application No. 60/319,488, filed on Aug. 23, 2002, provisional application No. 60/319,641, filed on Oct. 22, 2002.

(51) Int. Cl.
| | |
|---|---|
| A01N 63/00 | (2006.01) |
| A01N 1/02 | (2006.01) |
| C12N 5/00 | (2006.01) |
| C12N 5/07 | (2010.01) |
| C12N 5/10 | (2006.01) |
| C12N 5/071 | (2010.01) |

(52) U.S. Cl. .......... 424/93.71; 435/2; 435/363; 435/366; 435/372.2; 435/372.3; 435/325

(58) Field of Classification Search ................. None
See application file for complete search history.

(56) References Cited

U.S. PATENT DOCUMENTS

| | | |
|---|---|---|
| 683,690 A | 10/1901 | Johnson |
| 1,733,239 A | 10/1929 | Roberts |
| 1,961,700 A | 6/1934 | Moehler |
| 2,056,614 A | 10/1936 | Moehler |
| 2,212,230 A | 8/1940 | Goldmann |
| 2,212,330 A | 8/1940 | Thomas |
| 2,340,890 A | 2/1944 | Lang et al. |
| 2,417,143 A | 3/1947 | Tishler et al. |
| 2,786,014 A | 3/1957 | Tullis |
| 3,057,865 A | 10/1962 | Bardos et al. |
| 3,456,053 A | 7/1969 | Crawford |
| 3,629,071 A | 12/1971 | Sekhar |
| 3,683,177 A | 8/1972 | Veloz |
| 3,683,183 A | 8/1972 | Vizzini et al. |
| 3,705,985 A | 12/1972 | Manning et al. |
| 3,776,694 A | 12/1973 | Leittl |
| 3,852,032 A | 12/1974 | Urbach |
| 3,864,081 A | 2/1975 | Logrippo |
| 3,874,384 A | 4/1975 | Deindoerfer et al. |
| 3,894,236 A | 7/1975 | Hazelrigg |
| 3,926,556 A | 12/1975 | Boucher |
| 3,927,325 A | 12/1975 | Hungate et al. |
| 4,061,537 A | 12/1977 | Seiler et al. |
| 4,112,070 A | 9/1978 | Harmening |
| 4,124,598 A | 11/1978 | Hearst et al. |
| 4,139,348 A | 2/1979 | Swartz |
| 4,169,204 A | 9/1979 | Hearst et al. |
| 4,173,631 A | 11/1979 | Graham et al. |
| 4,181,128 A | 1/1980 | Swartz |
| 4,196,281 A | 4/1980 | Hearst et al. |
| 4,264,601 A | 4/1981 | Trachewsky |
| 4,267,269 A | 5/1981 | Grode et al. |
| 4,312,883 A | 1/1982 | Baccichetti et al. |
| 4,321,918 A | 3/1982 | Clark, II |
| 4,321,919 A | 3/1982 | Edelson |
| 4,336,809 A | 6/1982 | Clark |
| 4,381,004 A | 4/1983 | Babb |
| 4,390,619 A | 6/1983 | Harmening-Pittiglio |
| 4,398,031 A | 8/1983 | Bender et al. |

(Continued)

FOREIGN PATENT DOCUMENTS

EP          0066886          6/1982

(Continued)

OTHER PUBLICATIONS

Meunier et al., Photogenotoxicity of mammalian cells: A review of the different assays for In Vitro testing, Photochemistry and Photobiology, May 2002, pp. 1-17.*
Lindahl, T., Instability and decay of the primary structure of DNA. Nature, 362: 709-715, 1993.*
Joshi PC, Comparison of the DNA-damaging property of photosensitised riboflavin via singlet oxygen (1O2) and superoxide radical O2-. Mechanisms, Toxicol Lett. Aug. 1985;26(2-3):211-7.*
Lee et al., From leukocyte reduction to leukocyte transfusion: the immunological effects of transfused leukocytes, Bailliere's Clinical Haematology, vol. 13, No. 4, pp. 585-600.*
Lee et al., From leukocyte reduction to leukocyte transfusion: the immunological effects of transfused leukocytes, Bailliere's Clinical Haematology, vol. 13, No. 4, pp. 585-600, 2000.*
Truitt et al. (J. Immunology, 163 (9): 5145-5156 (1999)).*
Communication pursuant to Article 96(2) EPC from corresponding EP Application 03 751 901.4-1219, dated Oct. 20, 2006.
International Search Report for corresponding application PCT/US01/17875.
International Search Report for corresponding application PCT/US03/26770.

(Continued)

*Primary Examiner* — Suzanne M Noakes
*Assistant Examiner* — Jae W Lee
(74) *Attorney, Agent, or Firm* — Laura B. Arciniegas; Edna M. O'Connor; John R. Merkling

(57) ABSTRACT

A process for damaging and maintaining damage to the nucleic acids of pathogens such as white blood cells, bacteria and viruses which may be contained in blood or blood components. This process comprises adding to the blood or blood component containing pathogens an effective amount of riboflavin, and exposing the fluid to light of an appropriate wavelength to damage the nucleic acid of the pathogen and to substantially maintain the damage to the pathogenic nucleic acids to allow for subsequent transfusion into a recipient.

8 Claims, 8 Drawing Sheets

U.S. PATENT DOCUMENTS

| | | |
|---|---|---|
| 4,398,906 A | 8/1983 | Edelson |
| 4,402,318 A | 9/1983 | Swartz |
| 4,407,282 A | 10/1983 | Swartz |
| 4,421,987 A | 12/1983 | Herold |
| 4,424,201 A | 1/1984 | Valinsky et al. |
| 4,428,744 A | 1/1984 | Edelson |
| 4,432,750 A | 2/1984 | Estep |
| 4,456,512 A | 6/1984 | Bieler et al. |
| 4,457,918 A | 7/1984 | Holick et al. |
| 4,464,166 A | 8/1984 | Edelson |
| 4,467,206 A | 8/1984 | Taylor et al. |
| 4,474,153 A | 10/1984 | Hanamoto |
| 4,481,167 A | 11/1984 | Ginter et al. |
| 4,493,981 A | 1/1985 | Payne |
| 4,568,328 A | 2/1986 | King |
| 4,572,899 A | 2/1986 | Walker et al. |
| 4,573,960 A | 3/1986 | Goss |
| 4,573,961 A | 3/1986 | King |
| 4,573,962 A | 3/1986 | Troutner |
| 4,576,143 A | 3/1986 | Clark, III |
| 4,578,056 A | 3/1986 | King et al. |
| 4,585,735 A | 4/1986 | Meryman et al. |
| 4,596,547 A | 6/1986 | Troutner |
| 4,604,356 A | 8/1986 | Blake, II |
| 4,608,255 A | 8/1986 | Kahn et al. |
| 4,612,007 A | 9/1986 | Edelson |
| 4,613,322 A | 9/1986 | Edelson |
| 4,614,190 A | 9/1986 | Stanco et al. |
| 4,623,328 A | 11/1986 | Hartranft |
| 4,626,431 A | 12/1986 | Batchelor et al. |
| 4,642,171 A | 2/1987 | Sekine et al. |
| 4,645,649 A | 2/1987 | Nagao |
| 4,648,992 A | 3/1987 | Graf et al. |
| 4,649,151 A | 3/1987 | Dougherty et al. |
| 4,651,739 A | 3/1987 | Oseroff et al. |
| 4,675,185 A | 6/1987 | Kandler et al. |
| 4,683,195 A | 7/1987 | Mullis et al. |
| 4,683,202 A | 7/1987 | Mullis |
| 4,683,889 A | 8/1987 | Edelson |
| 4,684,521 A | 8/1987 | Edelson |
| 4,693,981 A | 9/1987 | Wiesehahn et al. |
| 4,695,460 A | 9/1987 | Holme |
| 4,704,352 A | 11/1987 | Miripol et al. |
| 4,708,715 A | 11/1987 | Troutner et al. |
| 4,726,949 A | 2/1988 | Miripol et al. |
| 4,727,027 A | 2/1988 | Wiesehahn et al. |
| 4,737,140 A | 4/1988 | Lee et al. |
| 4,748,120 A | 5/1988 | Wiesehahn |
| 4,769,318 A | 9/1988 | Hamasaki et al. |
| 4,775,625 A | 10/1988 | Sieber |
| 4,788,038 A | 11/1988 | Matsunaga |
| RE32,874 E | 2/1989 | Rock et al. |
| 4,828,976 A | 5/1989 | Murphy |
| 4,831,268 A | 5/1989 | Fisch et al. |
| 4,833,165 A | 5/1989 | Louderback |
| 4,861,704 A | 8/1989 | Reemtsma et al. |
| 4,866,282 A | 9/1989 | Miripol et al. |
| 4,878,891 A | 11/1989 | Judy et al. |
| 4,880,788 A | 11/1989 | Moake et al. |
| 4,915,683 A | 4/1990 | Sieber |
| 4,921,473 A | 5/1990 | Lee et al. |
| 4,930,516 A | 6/1990 | Alfano et al. |
| 4,946,438 A | 8/1990 | Reemtsma et al. |
| 4,948,980 A | 8/1990 | Wedekamp |
| 4,950,665 A | 8/1990 | Floyd |
| 4,952,812 A | 8/1990 | Miripol et al. |
| 4,960,408 A | 10/1990 | Klainer et al. |
| 4,961,928 A | 10/1990 | Holme et al. |
| 4,978,688 A | 12/1990 | Louderback |
| 4,986,628 A | 1/1991 | Lozhenko et al. |
| 4,992,363 A | 2/1991 | Murphy |
| 4,994,367 A | 2/1991 | Bode et al. |
| 4,998,931 A | 3/1991 | Slichter et al. |
| 4,999,375 A | 3/1991 | Bachynsky et al. |
| 5,011,695 A | 4/1991 | Dichtelmuller et al. |
| 5,017,338 A | 5/1991 | Surgenor |
| 5,020,995 A | 6/1991 | Levy |
| 5,030,200 A | 7/1991 | Judy et al. |
| 5,039,483 A | 8/1991 | Sieber et al. |
| 5,041,078 A | 8/1991 | Matthews et al. |
| 5,089,146 A | 2/1992 | Carmen et al. |
| 5,089,384 A | 2/1992 | Hale |
| 5,092,773 A | 3/1992 | Levy |
| 5,114,670 A | 5/1992 | Duffey |
| 5,114,957 A | 5/1992 | Hendler et al. |
| 5,120,649 A | 6/1992 | Horowitz et al. |
| 5,123,902 A | 6/1992 | Muller et al. |
| 5,133,932 A | 7/1992 | Gunn et al. |
| 5,147,776 A | 9/1992 | Koerner, Jr. |
| 5,149,718 A | 9/1992 | Meruelo et al. |
| 5,150,705 A | 9/1992 | Stinson |
| 5,166,528 A | 11/1992 | LeVay |
| 5,184,020 A | 2/1993 | Hearst et al. |
| 5,185,532 A | 2/1993 | Zabsky et al. |
| 5,192,264 A | 3/1993 | Fossel |
| 5,211,960 A | 5/1993 | Babior |
| 5,216,251 A | 6/1993 | Matschke |
| 5,229,081 A | 7/1993 | Suda |
| 5,232,844 A | 8/1993 | Horowitz et al. |
| 5,234,808 A | 8/1993 | Murphy |
| 5,236,716 A | 8/1993 | Carmen et al. |
| 5,247,178 A | 9/1993 | Ury et al. |
| 5,248,506 A | 9/1993 | Holme et al. |
| 5,250,303 A | 10/1993 | Meryman et al. |
| 5,258,124 A | 11/1993 | Bolton et al. |
| 5,269,946 A | 12/1993 | Goldhaber et al. |
| 5,273,713 A | 12/1993 | Levy |
| 5,281,392 A | 1/1994 | Rubinstein |
| 5,288,605 A | 2/1994 | Lin et al. |
| 5,288,647 A | 2/1994 | Zimlich, Jr. et al. |
| 5,290,221 A | 3/1994 | Wolf, Jr. et al. |
| 5,300,019 A | 4/1994 | Bischof et al. |
| 5,304,113 A | 4/1994 | Sieber et al. |
| 5,318,023 A | 6/1994 | Vari et al. |
| 5,340,716 A | 8/1994 | Ullman et al. |
| 5,342,752 A | 8/1994 | Platz et al. |
| 5,344,752 A | 9/1994 | Murphy |
| 5,344,918 A | 9/1994 | Dazey et al. |
| 5,358,844 A | 10/1994 | Stossel et al. |
| 5,360,734 A | 11/1994 | Chapman et al. |
| 5,366,440 A | 11/1994 | Fossel |
| 5,372,929 A | 12/1994 | Cimino |
| 5,376,524 A | 12/1994 | Murphy et al. |
| 5,378,601 A | 1/1995 | Gepner-Puszkin |
| 5,399,719 A | 3/1995 | Wollowitz et al. |
| 5,418,130 A | 5/1995 | Platz et al. |
| 5,419,759 A | 5/1995 | Naficy |
| 5,427,695 A | 6/1995 | Brown |
| 5,433,738 A | 7/1995 | Stinson |
| 5,459,030 A | 10/1995 | Lin et al. |
| 5,466,573 A | 11/1995 | Murphy et al. |
| 5,474,891 A | 12/1995 | Murphy |
| 5,482,828 A | 1/1996 | Lin et al. |
| 5,487,971 A | 1/1996 | Holme et al. |
| 5,494,590 A | 2/1996 | Smith et al. |
| 5,503,721 A | 4/1996 | Hearst et al. |
| 5,512,187 A | 4/1996 | Buchholz et al. |
| 5,516,629 A | 5/1996 | Park et al. |
| 5,527,704 A | 6/1996 | Wolf, Jr. et al. |
| 5,536,238 A | 7/1996 | Bischof |
| 5,545,516 A | 8/1996 | Wagner |
| 5,547,635 A | 8/1996 | Duthie, Jr. |
| 5,550,111 A | 8/1996 | Suhadolnik et al. |
| 5,556,958 A | 9/1996 | Carroll et al. |
| 5,556,993 A | 9/1996 | Wollowitz et al. |
| 5,557,098 A | 9/1996 | D'Silva |
| 5,559,250 A | 9/1996 | Cook et al. |
| 5,569,579 A | 10/1996 | Murphy |
| 5,571,666 A | 11/1996 | Floyd et al. |
| 5,578,736 A | 11/1996 | Wollowitz et al. |
| 5,585,503 A | 12/1996 | Wollowitz et al. |
| 5,587,490 A | 12/1996 | Goodrich, Jr. et al. |
| 5,593,823 A | 1/1997 | Wollowitz et al. |
| 5,597,722 A | 1/1997 | Chapman et al. |
| 5,607,924 A | 3/1997 | Magda et al. |
| 5,618,662 A | 4/1997 | Lin et al. |
| 5,622,867 A | 4/1997 | Livesey et al. |

| | | |
|---|---|---|
| 5,624,435 A | 4/1997 | Furumoto et al. |
| 5,624,794 A | 4/1997 | Bitensky et al. |
| 5,625,079 A | 4/1997 | Wollowitz et al. |
| 5,628,727 A | 5/1997 | Hakky et al. |
| 5,639,376 A | 6/1997 | Lee et al. |
| 5,639,382 A | 6/1997 | Brown |
| 5,643,334 A | 7/1997 | Eckhouse et al. |
| 5,652,096 A | 7/1997 | Cimino |
| 5,653,887 A | 8/1997 | Wahl et al. |
| 5,654,443 A | 8/1997 | Wollowitz et al. |
| 5,656,154 A | 8/1997 | Meryman |
| 5,656,498 A | 8/1997 | Iijima et al. |
| 5,658,530 A | 8/1997 | Dunn |
| 5,658,722 A | 8/1997 | Margolis-Nunno et al. |
| 5,683,661 A | 11/1997 | Hearst et al. |
| 5,683,768 A | 11/1997 | Shang et al. |
| 5,686,436 A | 11/1997 | Van Dyke |
| 5,688,475 A | 11/1997 | Duthie, Jr. |
| 5,691,132 A | 11/1997 | Wollowitz et al. |
| 5,698,524 A | 12/1997 | Mach et al. |
| 5,698,677 A | 12/1997 | Eibl et al. |
| 5,702,684 A | 12/1997 | McCoy et al. |
| 5,707,401 A | 1/1998 | Talmore |
| 5,709,653 A | 1/1998 | Leone |
| 5,709,991 A | 1/1998 | Lin et al. |
| 5,709,992 A | 1/1998 | Rubinstein |
| 5,712,085 A | 1/1998 | Wollowitz et al. |
| 5,712,086 A | 1/1998 | Horowitz et al. |
| 5,714,328 A | 2/1998 | Magda et al. |
| 5,736,313 A | 4/1998 | Spargo et al. |
| 5,739,013 A | 4/1998 | Budowsky et al. |
| 5,753,428 A | 5/1998 | Yuasa et al. |
| 5,756,553 A | 5/1998 | Iguchi et al. |
| 5,769,839 A | 6/1998 | Carmen et al. |
| 5,772,960 A | 6/1998 | Ito et al. |
| 5,783,093 A | 7/1998 | Holme |
| 5,789,150 A | 8/1998 | Margolis-Nunno et al. |
| 5,789,151 A | 8/1998 | Bitensky et al. |
| 5,789,601 A | 8/1998 | Park et al. |
| 5,798,238 A | 8/1998 | Goodrich, Jr. et al. |
| 5,798,523 A | 8/1998 | Villeneuve et al. |
| 5,817,519 A | 10/1998 | Zelmanovic et al. |
| 5,827,644 A | 10/1998 | Floyd et al. |
| 5,834,198 A | 11/1998 | Famulok et al. |
| 5,840,252 A | 11/1998 | Giertych |
| 5,843,459 A | 12/1998 | Wang et al. |
| 5,846,961 A | 12/1998 | Van Dyke |
| 5,854,967 A | 12/1998 | Hearst et al. |
| 5,866,074 A | 2/1999 | Chapman et al. |
| 5,869,701 A | 2/1999 | Park et al. |
| 5,871,900 A | 2/1999 | Wollowitz et al. |
| 5,876,676 A | 3/1999 | Stossel et al. |
| 5,899,874 A | 5/1999 | Jonsson |
| 5,906,915 A | 5/1999 | Payrat et al. |
| 5,908,742 A | 6/1999 | Lin et al. |
| 5,919,614 A | 7/1999 | Livesey et al. |
| 5,922,278 A | 7/1999 | Chapman et al. |
| 5,935,092 A | 8/1999 | Sun et al. |
| 5,955,256 A | 9/1999 | Sowemimo-Coker et al. |
| 5,955,257 A | 9/1999 | Burger et al. |
| 5,965,349 A | 10/1999 | Lin et al. |
| 5,972,593 A | 10/1999 | Wollowitz et al. |
| 5,976,884 A | 11/1999 | Chapman et al. |
| 5,981,163 A | 11/1999 | Horowitz et al. |
| 6,004,741 A | 12/1999 | Wollowitz et al. |
| 6,004,742 A | 12/1999 | Wollowitz et al. |
| 6,017,691 A | 1/2000 | Wollowitz et al. |
| 6,020,333 A | 2/2000 | Berque |
| 6,060,233 A | 5/2000 | Wiggins |
| 6,063,624 A | 5/2000 | Kandler et al. |
| 6,077,659 A | 6/2000 | Ben-Hur et al. |
| 6,087,141 A | 7/2000 | Margolis-Nunno et al. |
| 6,093,725 A | 7/2000 | Cook et al. |
| 6,106,773 A | 8/2000 | Miekka et al. |
| 6,133,460 A | 10/2000 | Wollowitz et al. |
| 6,143,490 A | 11/2000 | Cook et al. |
| 6,171,777 B1 | 1/2001 | Cook et al. |
| 6,177,441 B1 | 1/2001 | Cook et al. |
| 6,194,139 B1 | 2/2001 | Wollowitz et al. |
| 6,197,207 B1 | 3/2001 | Chapman et al. |
| 6,214,534 B1 | 4/2001 | Horowitz et al. |
| 6,218,100 B1 | 4/2001 | Wollowitz et al. |
| 6,258,319 B1 | 7/2001 | Hearst et al. |
| 6,258,577 B1 * | 7/2001 | Goodrich et al. .......... 435/173.3 |
| 6,268,120 B1 | 7/2001 | Platz et al. |
| 6,270,952 B1 | 8/2001 | Cook et al. |
| 6,277,337 B1 | 8/2001 | Goodrich et al. |
| 6,410,219 B1 | 6/2002 | Cook et al. |
| 6,413,714 B1 | 7/2002 | Margolis-Nunno et al. |
| 6,420,570 B1 | 7/2002 | Wollowitz et al. |
| 6,433,343 B1 | 8/2002 | Cimino et al. |
| 6,455,286 B1 | 9/2002 | Wollowitz et al. |
| 6,461,567 B1 | 10/2002 | Hearst et al. |
| 6,469,052 B2 | 10/2002 | Wollowitz et al. |
| 6,503,699 B1 | 1/2003 | Wollowitz et al. |
| 6,514,987 B1 | 2/2003 | Cook et al. |
| 6,544,727 B1 | 4/2003 | Hei |
| 6,565,802 B1 | 5/2003 | Hanley et al. |
| 6,576,201 B1 | 6/2003 | Woo et al. |
| 6,586,749 B2 | 7/2003 | Cimino et al. |
| 6,596,230 B1 | 7/2003 | Woo et al. |
| 6,680,025 B2 | 1/2004 | Hearst et al. |
| 6,686,480 B2 | 2/2004 | Wollowitz et al. |
| 2002/0022215 A1 | 2/2002 | Sobsey et al. |

FOREIGN PATENT DOCUMENTS

| | | |
|---|---|---|
| EP | 0124363 | 4/1984 |
| EP | 0108588 | 5/1984 |
| EP | 0196515 | 3/1986 |
| EP | 0184331 | 6/1986 |
| EP | 0491757 | 9/1990 |
| EP | 0525 138 | 12/1991 |
| EP | 0590514 | 4/1994 |
| EP | 0679398 | 11/1995 |
| EP | 0510185 | 12/1996 |
| EP | 0754461 | 1/1997 |
| EP | 0801072 | 10/1997 |
| FR | 2674753 | 10/1992 |
| FR | 2715303 | 7/1995 |
| FR | 2718353 | 10/1995 |
| GB | 2034463 | 6/1980 |
| WO | WO83/02328 | 7/1983 |
| WO | WO85/02116 | 5/1985 |
| WO | WO88/10087 | 12/1988 |
| WO | WO89/06702 | 7/1989 |
| WO | WO90/00059 | 1/1990 |
| WO | WO90/10461 | 9/1990 |
| WO | WO91/02529 | 3/1991 |
| WO | WO92/08349 | 5/1992 |
| WO | WO92/28348 | 5/1992 |
| WO | WO92/11057 | 7/1992 |
| WO | WO92/17173 | 10/1992 |
| WO | WO94/07426 | 4/1994 |
| WO | WO94/07499 | 4/1994 |
| WO | WO95/02325 | 1/1995 |
| WO | WO95/11028 | 4/1995 |
| WO | WO95/12973 | 5/1995 |
| WO | WO95/16348 | 6/1995 |
| WO | WO96/14740 | 5/1996 |
| WO | WO96/14741 | 5/1996 |
| WO | WO97/07674 | 3/1997 |
| WO | WO97/18844 | 5/1997 |
| WO | WO97/22245 | 6/1997 |
| WO | WO97/36581 | 10/1997 |
| WO | WO97/36634 | 10/1997 |
| WO | WO98/22150 | 5/1998 |
| WO | WO98/30545 | 7/1998 |
| WO | WO98/31219 | 7/1998 |
| WO | WO98/41087 | 9/1998 |
| WO | WO98/51147 | 11/1998 |
| WO | WO99/11305 | 3/1999 |
| WO | WO00/04930 | 2/2000 |
| WO | WO00/11946 | 9/2000 |
| WO | WO01/28599 | 4/2001 |
| WO | WO02/02153 | 1/2002 |
| WO | WO02/30190 | 4/2002 |
| WO | WO/02/96471 * | 5/2002 |

OTHER PUBLICATIONS

Abdursashidova et al, "Polynucleotide-protein interactions in the translation system. Identification of proteins interacting with tRNA in the A- and P-sites of *E. coli* ribosomes," 1979 *Nucleic Acids Res.* 6(12):3891-3909.

Belikov et al, "Choice of an Effective Method of Analysis of Riboflavin and Stud of its Stability", DrugU, AN 1988, 37(2), Suppl. S26, 1988-39621.

Benade et al, "Inactivation of free and cell-associated human immunodeficiency virus in platelet suspensions by aminomethyltrimethylpsoralen and ultraviolet light", *Transfusion*, vol. 34, No. 8, 1994, pp. 680-684.

Brodie et al, "Mode of Action of Vitamin K in Microorganisms," 1966, *Vitam. Horm* 24:447-463.

Budowsky et al, "Induction of polynucleotide-protein cross-linkages by ultraviolet irradiation," 1986, *Eur. J. Biochem.* 159:95-101.

Budowsky et al, "Polynucleotide-Protein Cross-Links Induced by Ultraviolet Light and Their Use for Structural Investigation of Nucleoproteins," 1989, *Progress in Nucleic Acid Res. and Mol. Bio* 37:1-65.

Budowsky et al, "Preparation of cyclic 2',3'-monophosphates of oligoadenylates (A2'p)nA>p and A3'p(A2'p)n-1A<, p." 1994, *Eur. J. Biochem.* 220:97-104.

Budowsky et al, "Principles of selective inactivation of viral genome. VIII, The influence of β-propiolactone on immunogenic and protective activities of influenza virus," 1993, *Vaccine* 11(3):343-348.

Budowsky et al, "Principles of selective inactivation of viral genome. VI, Inactivation of the infectivity of the influenza virus by the action of β-propiolactone," 1991, *Vaccine* 9:398-402.

Budowsky et al, "Principles of selective inactivation of viral genome. VII, Some peculiarities in determination of viral suspension infectivity during inactivation by chemical agents," 1991, *Vaccine* 9:473-476.

Budowsky, EI, "Problems and Prospects for Preparation of Killed Antiviral Vaccines", 1991, *Adv. Virus Res.* 39:255-290.

Cadet et al., "Mechanisms and Products of Photosensitized Degradation of Nucleic Acids and Related Model Compounds," 1983, *Israel J. Chem.* 23:420-429.

Chow et al., "Recognition of G-U mismatches by tris(47-diphenyl-110-phenanthroline)rhodium(III)," 1992 *Biochemistry* 31(24):5423-5429.

Corash et al, "Use of 8-Methoxypsoralen and long wavelength ultraviolet radiation for decontamination of platelet concentrates", *Blood Cells*, 1992, 18:57-74.

Corash, L, "Inactivation of Viruses, Bacteria, Protozoa, and Leukocytes in Platelet Concentrates", *Vox Sanguinis*, 1998; 74 (suppl. 2): 173-176.

Deutsch, E. "Vitamin K in Medical Practice: Adults," 1966, *Vitam. Horm.*, 24:665-680.

Dodd et al, "Inactivation of Viruses in platelet suspensions that retain their in vitro characteristics: comparison of psoralen-ultraviolet A and merocyanine 540-visible light methods", *Transfusion*, vol. 31, No. 6, 1991, pp. 483-490.

Dodd, RY, "Viral inactivation in platelet concentrates", *TCB*, 1994, 3:181-186.

Ennever et al, "Short Communication Photochemical Reactions of Riboflavin: Covalent Binding in DNA and to Poly (dA)□Poly (dT)," 1983 *Pediatr. Res.* 17:234-236.

Friedman et al, "Reducing the Infectivity of Blood Components—What we have learned", 1995, *Immunological Investigations* 24 1&2: 49-71.

Gasparro, F.P., "Symposium-in-Print: Psoralen Photobiology: Recent Advances", *Photochemistry and Photobiology*, 1996, 63(5):553-557.

Ghiron et al, "The Flavin-sensitized Photoinactivation of Trypsin," 1965, *Photochemistry and Photobiology* 4:13-26.

Goodrich et al, "The design and development of selective, photoactivated drugs for sterilization of blood products," 1997, *Drugs of the Future* 22(2):159-171.

Hanson, C.V., "Photochemical Inactivation of Viruses with Psoralens: An Overview", *Blood Cells*, 1992, 18:7-25.

Hanson, CV, "Photochemical Inactivation of Deoxyribonucleic and Ribonucleic Acid Viruses by Chlorpromazine", *Antimicrob. Agent Chemother.*, 1979, 15(3), pp. 461-464.

Hei et al, "Elimination of cytokine production in stored platelet concentrate aliquots by photochemical treatment with psoralen plus ultraviolet A light", *Transfusion*, vol. 39, 1999, pp. 239-248.

Heinmets et al, "Inactivation of Viruses in Plasma by Photosensitized Oxidation", Walter Reed Army Institute of Research, Nov. 1955, pp. 1-16.

Hoffmann et al "DNA Strand Breaks in mammalian Cells Exposed to Light in the Presence of Riboflavin and Tryptophan," *Photochemistry and Photobiology*, vol. 29 pp. 299-303 (1979).

Hogman, Claes, "Leucocyte Depletion of Blood Components", p. 1-4.

Isaacs et al, "Synthesis and Characterization of New Psoralen Derivatives with Superior Photoreactivity with DNA and RNA", *Biochemistry*, vol. 16, No. 6, 1977, pp. 1058-1064.

Ivanchenko et al, "The photochemistry of purine components of nucleic acids. I. The efficiency of photolysis of adenine and guanine derivatives in aqueous solution,", 1974, *Nucleic Acids Res.* 2(8):1365-1373.

Joshi, P.C., "Comparison of the DNA-damaging property of photosensitized riboflavin via singlet oxygen (1O2) and superoxide radical (Oi) mechanisms," (1985) *Toxicology Letters* 26:211-217.

Kabuta et al. (1978), "Inactivation of viruses by dyes and visible light," *Chem. Abstracts* 87(1), Abstract No. 400626.

Kale et al. (1992), "Assessment of the genotoxic potential of riboflavin and lumiflavin; B. Effect of light," *Mutation Res.* 298:17-23.

Klebanoff et al, "The risk of Childhood Cancer after Neonatal Exposure of Vitamin K," 1993, *New Eng. J. Med*, 329(13):905-908.

Kobayashi et al. (1983), "The molecular mechanism of mutation. Photodynamic action of flavins on the RNA-synthesizing system," *Chem. Abstracts* 98(1), Abstract No. 1200.

Korycka et al, "Photodegradation of DNA with fluorescent light in the presence of riboflavin, and photoprotection by flavin triplet-state quenchers," (1980) *Biochimica et Biophysica Acta* 610:229-234.

Kovalsky et al, "Laser (Two-Quantum) Photolysis of Polynucleotides and Nucleoproteins: Quantitative Processing of Results," 1990 *Photochemistry and Photobiology* 5(6):1659-665.

Kuratomi et al, "Studies on the Interactions Between DNA and Flavins," (1977) *Biochemica et Biophysica Acta* 476:207-217.

Leontis et al, "The 5SrRNA loop E: Chemical probing and phylogenetic data versus crystal structure", 1998, *RNA* 4:1134-1153.

Lim et al, "Chemical probing of tDNAPhewith transition metal complexes: a structural comparison of RNA and DNA," 1993, *Biochemistry* 32:11029-11034.

Lin et al, "Use of 8-Methoxypsoralen and Long-Wavelength Ultraviolet Radiation for Decontamination of Platelet Concentrates", *Blood*, vol. 74, No. 1, 1989, pp. 517-525.

Maddox, J., "The working of vitamin K," (1991) *Nature* 353(6346):695.

Malik et al, "New Trends in Photobiology—Bactericidal Effects of Photoactivated Porhyrins—an Alternative Approach to Antimicrobial Drugs," *J. Photochem. Photobiol* Pt.B: Biology, 1990, V:281-293.

Matthews et al., "Photodynamic therapy of viral contaminants with potential for blood banking application," (1988) *Transfusion* 28(1):81-83.

McCord, EF, "Chemically induced dynamic nuclear polarization studies of yeast", 1984, *Biochemistry* 23:1935-1939.

Merenstein et al, (Vitamin K ad Hoc Task Force), "Controversies concerning vitamin K and the newborn," 1993, *Pediatrics* 901(5):1001-1005.

Merrifield et al, Vitamin K as a fungistatic agent, 1965, *Appl. Microbio.* 13(5):660-662.

Merrifield et al, "Factors affecting the antimicrobial acitivity of Vitamin K5," 1965, *Appl. Microbio.* 13(5):766-770.

Moroff et al, "Factors Influencing Virus Inactivation and Retention of Platelet Properties Following Treatment with Aminomethyltrimethylpsoralen and Ultraviolet A Light", *Blood Cells*, 1992, 18:43-56.

Murata et al., "Effect of vitamins other than vitamin C on viruses: virus-inactivating activity of vitamin K5" (1983) *J. Nutr. Sci. Vitaminol* (Tokyo) 29(6):721-724.

Naseem et al., "Effect of alkylated and intercalated DNA on the generation of superoxide anion by riboflavin," (1988) *Bioscience Reports* 8(5):485-492.

North et al, "Photosensitizers as Virucidal Agents", *J. Photochem. Photobiol.*, 1993, 17(2), pp. 99-108.

Peak et al., "DNA Breakage Caused by 334-nm Ultraviolet Light is Enhanced by Naturally Occurring Nucleic Acid Components and Nucleotide Coenzymes," 1984 *Photochemistry and Photobiology* 39(5):713-716.

Piette et al., "Alteration of Guanine Residues During Proflavine Mediated Photosensitization of DNA," (1981) *Photochemistry and Photobiology* 33:325-333.

Piette et al., "Production of Breaks in Single- and Double-Stranded Forms of Bacteriophage ‖X174 DNA by Proflavine and Light Treatment," (1979) *Photochemistry and Photobiology* 30:369-378.

Pratt et al, "Vitamin K5 as an Antimicrobial Medicament and Preseravative", 1950, *J. Am. Pharm. Assn* 39(3):127-134.

Prodouz et al, "Effects of Two Viral Inactivation Methods on Platelets: Laser-UV Radiation and Merocyanine 540-Mediated Photoinactivation", *Blood Cells*, 1992, 18:101-116.

Prodouz et al, "Inhibition by albumin of merocyanine 540-mediated photosensitization of platelets and viruses", *Transfusion*, vol. 31, No. 3, 1991, pp. 415-422.

Product Advertisement for "Ultracure 100SS Plus Specifications," EFOS USA, Williamsville, NY, USA.

Ramu et al, "The Riboflavin-Mediated Photoxidation of Oxorubicin", Cancer Chemother. Pharrnacol, 2000, 46(6), 449-458.

Reinhardt et al, "Virucidal activity of retinal," *Antimicrobial Agents and Chemotherapy* 16:3, Sep. 1979, p. 421-423.

Schwartzman, G., "Antibacterial Properties of 4-Amino-2-Methyl-1-Naphthol Hydrocloride," 1948, Proc. *Soc. Exp. Biol. Med*. 67:376-378.

Simukova et al, "Conversion of Non-covalent Interactions in Nucleoproteins into Covalent Bonds: UV-Induced Formation of Polynucleotide-Protein Crosslinks in Bacteriophage Sd Virions," 1974, *FEVS Letters* 38(3):299-303.

Speck et al., "Further Observations on the Photooxidation of DNA in the Presence of Riboflavin," (1976) *Biochimica et Biphysica Acta* 435:39-44.

Spranger, J. "Does vitamin K cause cancer?" 1993, *Eur. J. Pediatr.* 152(2):174.

Stassinopoulos et al, "Helinx Technology, Utilized in the Intercept Blood System, Effectively Inactivates *Deinoccus radiodurans*, a Bacterium with Highly Efficient DNA Repair", Abstract presented at the 44th Annual Meeting of the American Society of Hematology, 2002, *Blood* 100(11)(part 2 of 2): p. 708a, 2002, Abstract #2790.

Tsugita, et al., "Photosensitized inactivation of ribonucleic acids in the presence of riboflavin," (1965) *Biochim. Biophys. Acta* 103:360-363.

Uehara et al, "Effect of adenine on the riboflavin-sensitized photoreaction. II. Effect of adenine on the photodynamic inactivation of transforming deoxyribonucleic acid in the presence of riboflavin", 1972, *J Biochemistry*, 71:5, 805-810.

Uehara et al, "Effect of adenine on the riboflavin-sensitized photoreaction. I. Effect of adenine on the photodynamic inactivation of yeast alcohol dehydrogenase in the presence of riboflavin," *J. Vitaminology*, 17:3,1971,148-154.

Vest, M., "Vitamin K in medical practice; pediatrics," 1966, *Vitami. Horm.* 24:649-663.

Way et al, "HPLC Analysis of Riboflavin and its Photodegradation Products in an Intravenous Infusions Formulation", *Pharm. Res.*, 7(9), Suppl, S26, *DrugU, AN* 1991-11544.

Webb et al, "Mutagenesis in *Escherichia coli* by Visible Light," 1967, *Science* 156:1104-1105.

Yang et al, "Vitamin K5 as a Food Preservative," *1958 Food Technology* 501-504.

\* cited by examiner

Flow TACS DNA Fragmentation Assay with PET treated Human Jurkat T cells

| treatment | Day 1 | | Day 2 | |
| --- | --- | --- | --- | --- |
| | # of cells | % positive | # of cells | % positive |
| Saline/UV (7J/cm2) | 345 | 85.5 | 3780 | 0.4 |
| Rf/UV (5J/cm2) | 465 | 36.1 | 1425 | 87.5 |
| Saline/Vis (60min) | 630 | 1.2 | 2865 | 1.6 |
| Rf/Vis (20min) | 1020 | 44.6 | 10000 | 40.6 |

*Figure 4*

INDUCTION OF AND MAINTENANCE OF NUCLEIC ACID DAMAGE IN PATHOGENS USING RIBOFLAVIN AND LIGHT

PRIORITY CLAIM

This application is a continuation of U.S. application Ser. No. 10/377,524 filed Feb. 28, 2003, which is a continuation of U.S. application Ser. No. 09/586,147 filed Jun. 2, 2000, now abandoned; and claims the benefit of U.S. Provisional Application No. 60/319,488 filed Aug. 23, 2002; and U.S. Provisional Application No. 60/319,641 filed Oct. 22, 2002.

BACKGROUND

Whole blood collected from volunteer donors for transfusion into recipients is typically separated into its components: red blood cells, white blood cells, platelets, plasma and plasma proteins, by apheresis or other known methods. Each of these blood components are typically stored individually and are used to treat a multiplicity of specific conditions and disease states. For example, the red blood cell component is used to treat anemia, the concentrated platelet component is used to control bleeding, and the plasma component is used frequently as a source of Clotting Factor VIII for the treatment of hemophilia.

After the components are separated, the white blood cell component is typically discarded, unless the cells are needed for specific applications such as photoimmune therapy or photophoresis. Cell separation procedures are not 100% effective. There is unusually some small percentage of other types of cells which are carried over into a separated blood component. Undesirable cells are typically cells of a different type which are carried over in some percentage into a desirable component. Cells such as white blood cells, which may transmit infections including HIV and CMV as well as causing other transfusion-related complications such as Graft vs. Host Disease and alloimmunization are considered undesirable. Ways to reduce the risks of these transfusion related complications from white blood cells is either to reduce the number of white blood cells transfused into a recipient, and/or to effectively destroy the viability and capacity of any transfused white blood cells to function post transfusion. White blood cells include granulocytes, monocytes and lymphocytes.

Current methods used to deplete contaminating white blood cells in blood products to be transfused include leukocyte filtration, UV irradiation of platelet concentrates and gamma irradiation of red blood cells and platelet concentrates. These methods do not completely eliminate the white blood cells however, and gamma and UV irradiation affect the cell quality of desired blood components such as platelets and red blood cells.

The blood or blood component to be transfused may also be contaminated with microorganisms which may cause infections or unwanted immune reactions in the transfusion recipient. Microorganisms which may be present include, but are not limited to, viruses, (both extracellular and intracellular), bacteria, fungi, blood-transmitted parasites and protozoa.

Photosensitizers, or compounds which absorb light of a defined wavelength and transfer the absorbed energy to an electron acceptor may be a solution to the above problems, by inactivating pathogens contaminating a blood product without damaging the desirable components of blood. For the purposes of this invention, the general term "pathogen" may encompass any undesirable organism which may be found in blood or a blood product. Pathogens may be undesirable cells such as white blood cells, or may include microorganisms such as bacteria, parasites or viruses.

There are many pathogen reduction compounds known in the art to be useful for inactivating microorganisms or other infectious particles. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones.

Dardare et al. showed in a study of the binding affinities of several common photosensitizers that both psoralen and methylene blue substantially bind to nucleic acids, phospholipid membranes and proteins in typical pathogen eradication experiments.

Although many publications have shown that damage to nucleic acids can be caused by photosensitizers and light, the issue of whether induction of damage to the nucleic acids of pathogens and undesirable cells is maintained over time, and after the pathogen reduced cells have been infused into a recipient has not been addressed.

One study done by R. Mababagloob et al. looked to see what effect S-59 and S-303 (psoralens) had on the DNA repair mechanisms of *D. radiodurans*, a bacteria which has multiple genomic copies and redundant repair mechanisms. The authors found that the above treatment in combination with UVA light or change in pH, resulted in 1 S-303 adduct for every 114 genomic DNA base pairs and 1 S-59 adduct for every 58 genomic DNA base pairs. However, this study did not examine whether the damage to the DNA was maintained after treatment, or was repaired by the bacteria. (Mababangloob, R., Castro, G., Stassinopoulos, A.; Helinx Technology, Utilized in the Intercept Blood System, Effectively Inactivates *Deinoccus radiodurans*, a Bacterium with Highly Efficiently DNA Repair; Abstract presented at the 44$^{th}$ Annual Meeting of the American Society of Hematology, 2002).

It is towards the method of pathogen reducing blood and blood components by inducing permanent damage to the nucleic acids of pathogens that the present invention is directed. Permanent damage means that the inactivated pathogens are unable to re-activate upon storage or upon infusion into a patient.

SUMMARY

The present invention is directed towards a method of substantially inactivating pathogens such as white blood cells, and microorganisms such as bacteria and viruses which may be present in a fluid to be transfused into a recipient. The invention is for a process for substantially maintaining damage to pathogen nucleic acid caused by a photosensitizer and light in a fluid containing pathogens and blood components comprising the steps of adding to the fluid a photosensitizer comprising riboflavin; irradiating the fluid and photosensitizer with light at an appropriate wavelength to activate the riboflavin to cause damage to the nucleic acid of the pathogen; and substantially maintaining the damage to the pathogen nucleic acid during storage and/or after transfusion of the fluid into a recipient.

BRIEF DESCRIPTION OF THE DRAWINGS

FIG. 4 is a table showing fragmentation of Jurkat cell DNA over a two day period following treatment with riboflavin and either UV or visible light.

FIG. 6b is a graph which quantifies the percentage of intact (not fragmented) DNA from the gel shown in 6a.

DETAILED DESCRIPTION OF THE INVENTION

Figure 1:
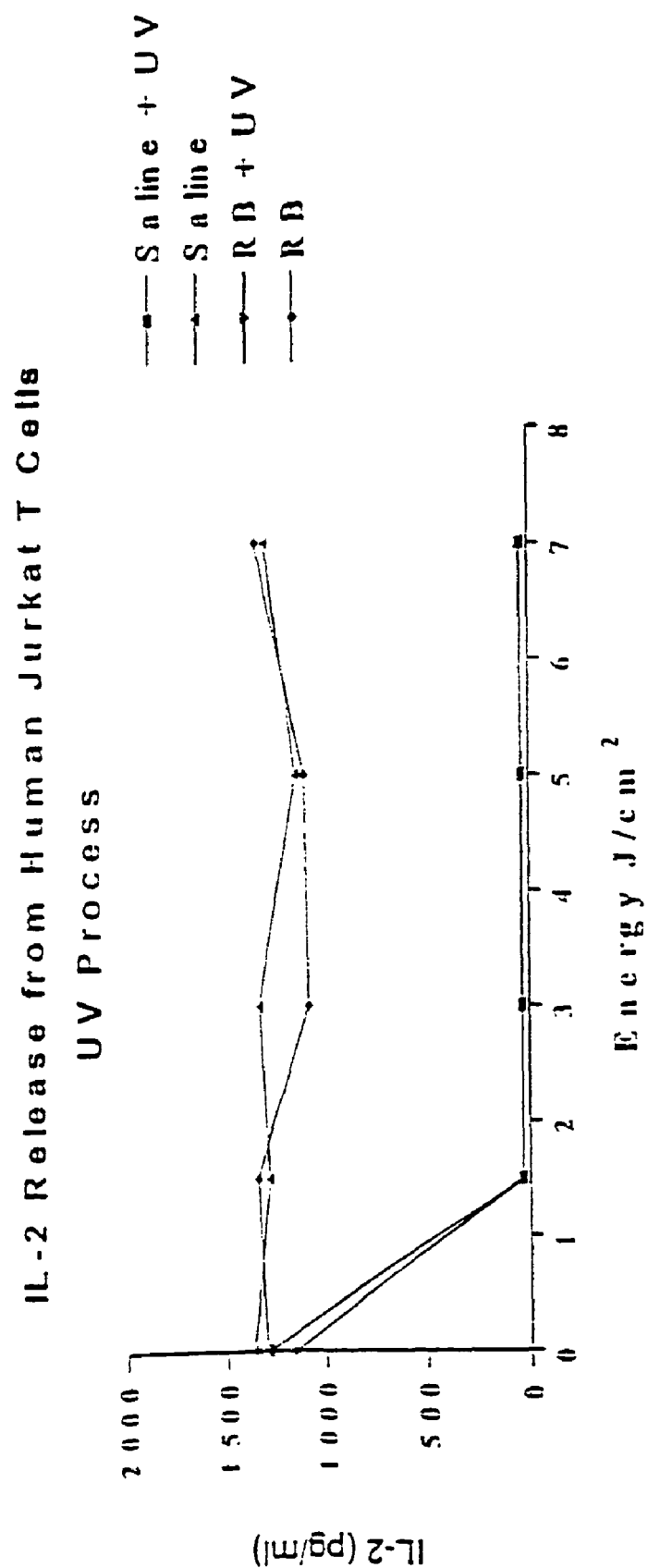
FIG. 1 is a graph showing the production of IL-2 from Jurkat cells after treatment with riboflavin and UV light.

A "photosensitizer" useful in this invention is defined as any compound which absorbs radiation at one or more defined wavelengths and subsequently utilizes the absorbed energy to carry out a chemical process. In this case, the desired photosensitizer will bind to any nucleic acids which are present in the fluid to be decontaminated to which the photosensitizer has been added. The chemical processes which occur damage any nucleic acids which may be in the fluid. The fluid may contain blood or blood products, or may be a solvent which requires sterility.

Endogenous photosensitizers are preferred for use in this invention. The term "endogenous" means naturally found in a human or mammalian body, either as a result of synthesis by the body or because of ingestion as an essential foodstuff (e.g. vitamins) or formation of metabolites and/or byproducts in vivo. When endogenous photosensitizers are used, particularly when such photosensitizers are not inherently toxic or do not yield toxic photoproducts after photoradiation, no removal or purification step is required after decontamination, and the decontaminated product can be directly returned to a patient's body or administered to a patient in need of its therapeutic effect.

Examples of such endogenous photosensitizers which may be used in this invention are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]) and alloxazine mononucleotide (also known as flavine mononucleotide [FMN] and riboflavine-5-phosphate). The term "alloxazine" includes isoalloxazines.

Use of endogenous isoalloxazines as a photosensitizer to pathogen reduce blood and blood components are described in U.S. Pat. Nos. 6,258,577 and 6,277,337 both issued to Goodrich et al., and are herein incorporated by reference to the amount not inconsistent.

Endogenously-based derivative photosensitizers include synthetically derived analogs and homologs of endogenous photosensitizers which may have or lack lower (1-5) alkyl or halogen substituents of the photosensitizers from which they are derived, and which preserve the function and substantial non-toxicity thereof. Such endogenously-based derivative photosensitizers which may be used in this invention are disclosed in U.S. Pat. No. 6,268,120 to Platz et al., which discloses alloxazine derivatives which may also be used to inactivate microorganisms contained in blood or blood components. This patent is incorporated by reference into the present invention to the amount not inconsistent herewith.

The photosensitizer compound riboflavin (7,8-dimethyl-10-ribityl isoalloxazine) has been reported to attack nucleic acids. Nucleic acids include both deoxyribonucleic acids and ribonucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360-363; and Speck, W. T. et al. (1976), "Further Observations on the Photooxidation of DNA in the Presence of Riboflavin," Biochimica et Biophysica Acta 435:39-44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207-217. Hoffmann, M. E., et al. (1979), DNA strand breaks upon exposure to proflavine and light are reported in Piette, J. et al. (1979), "Production of Breaks in Single- and Double-Stranded Forms of Bacteriophage ΦX 174 DNA by Proflavine and Light Treatment," Photochemistry and Photobiology 30:369-378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325-333.

What has not been previously known or explored prior to the instant invention, is whether the strand breaks in the nucleic acids caused by the photolysis of riboflavin is permanent. That is, whether the nucleic acid repair mechanisms of the pathogen are unable to repair the damage caused by riboflavin and light and therefore prevent the pathogen from replicating. In this context, repair is defined as the molecular processes that are the basis for pathogen reactivation. Reactivation, or the synonymous term recovery, is defined as the regaining of, by a damaged pathogen, the capability to propagate and to form a colony.

Substantially maintaining the damage means that any damage sustained by the nucleic acids of pathogens is maintained over time so that when the blood product, which has been treated with riboflavin and light is transfused into a recipient, the inactivated pathogen will not self-repair the damaged nucleic acids, and reproduce in the transfusion recipient. Transfusion related complications caused by viable pathogens which may be contained in the pathogen reduced blood or blood product will therefore be substantially reduced.

The method of this invention requires mixing the photosensitizer with the whole blood or with the separated blood component to be decontaminated. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate any pathogenic nucleic acids which may be present in the fluid, but less than a toxic (to the desired components) or insoluble amount. If riboflavin is used as the photosensitizer, it may be added to the fluid at a final concentration of between about 50-500 µM. Pathogenic nucleic acid includes any undesirable nucleic acid such as nucleic acid from white blood cells, bacteria or viruses. Nucleic acids include either deoxyribonucleic acid (DNA), ribonucleic acid (RNA) or both.

The fluid containing the photosensitizer is exposed to light of the appropriate wavelength to activate the photosensitizer and to cause substantially permanent damage to the pathogenic nucleic acids. The pathogen reduced fluid may then be stored for a period of time before being transfused into a recipient, or may be transfused into a recipient directly after the pathogen reduction procedure.

Example 1

To determine the effectiveness of isoalloxazine (riboflavin) photosensitizer and light in damaging and maintaining the damage to nucleic acids of white blood cells that may be contained in a solution of red blood cells or platelets, Jurkat cells (a model T-lymphocytic cell line) were spiked into solutions containing either red blood cells or platelets. Jurkat cells were initially grown in RPMI cell growth medium at 37° C. in 5% $CO_2$.

Set forth below is one protocol which may be used in this invention for determining the effectiveness of riboflavin and light in causing damage to and subsequently maintaining the damage to the nucleic acids of any contaminating white blood cells in a solution containing red blood cells.

Fluid containing red blood cells and having 5% plasma carryover may be placed into any container known in the art. A 1 L bag is one such example, not meant to be limiting. A quencher may also be optionally added to the fluid. Such quenchers may include antioxidants or other agents to prevent damage to desired fluid components or to improve the rate of inactivation of microorganisms. Quenchers useful in this invention are exemplified by glutathione, n-acetyl-cysteine, cysteine, adenine, histidine, tyrosine, tryptophan, ascorbate, vitamin E, trolox, TPGS and mixtures thereof. Riboflavin was added to the cells at a final concentration of 500 µM either with the quencher (if optionally added) or separately. Any means known in the art for adding the photosensitizer to the fluid to be decontaminated and for placing the fluid in the container may be used. Such means typically include flow conduits, ports, reservoirs, valves, and the like. Additives which enhance blood component viability after treatment with riboflavin and light may also be added either pre or post illumination. Examples of additives which may be added to the fluid may include methylxanthines and/or PGE1.

Air was added to the fluid containing red blood cells and riboflavin at a volume of 133 mL for every 266 mL of fluid. Air may be added to the fluid contained in the bag by any means known in the art. The fluid containing red cells was then "spiked" with Jurkat cells at a concentration of $10^6$/mL to simulate white blood cell carryover in a collection procedure. The fluid containing red blood cells and spiked Jurkat cells was illuminated with light in the visible (from a source having a peak emission at 447 nm) spectrum at an intensity of 190 $J/cm^2$. Treated cells and untreated controls were incubated for 24 hours at 37° C. in growth medium to assess long term survival of cells which were not killed during the illumination process. After treatments, the Jurkat cells were recovered and assayed for cell viability markers, such as production of IL-2, cell proliferation and fragmentation of DNA.

A similar protocol was used to determine the effectiveness of inactivating white blood cells and maintaining the inactivation of the cells in a solution containing platelets. A final concentration of 50 µM isoalloxazine was added to platelets collected by apheresis with a 90% plasma carryover. The fluid containing platelets was "spiked" with Jurkat cells at a concentration of $10^6$/mL to simulate white blood cell contamination. The fluid containing platelets and spiked Jurkat cells was illuminated with light in the ultraviolet (UV) spectrum at 320 nm and an intensity of 7 $J/cm^2$. After treatments, the Jurkat cells were recovered and assayed for markers of cell viability, such as production of IL-2, cell proliferation and fragmentation of DNA.

Jurkat cell death was assessed with the Molecular Probes Live/Dead Cytotoxicity/viability assay. Cells were exposed to a staining solution containing ethidium homodimer-1 which stains non-viable (dying or dead) cells orange/red and calcein AM which stains viable (live) cells green. Cells with holes in their membrane appear red/orange when stain is excited with 495 nm light. Intact cells stain green. Cells that appear orange and that contain no green are counted as dead cells; green cells that contain no orange stain are counted as live. Dead cells in a sample are expressed as a percentage of the total number of cells present in a sample.

Figure 2:
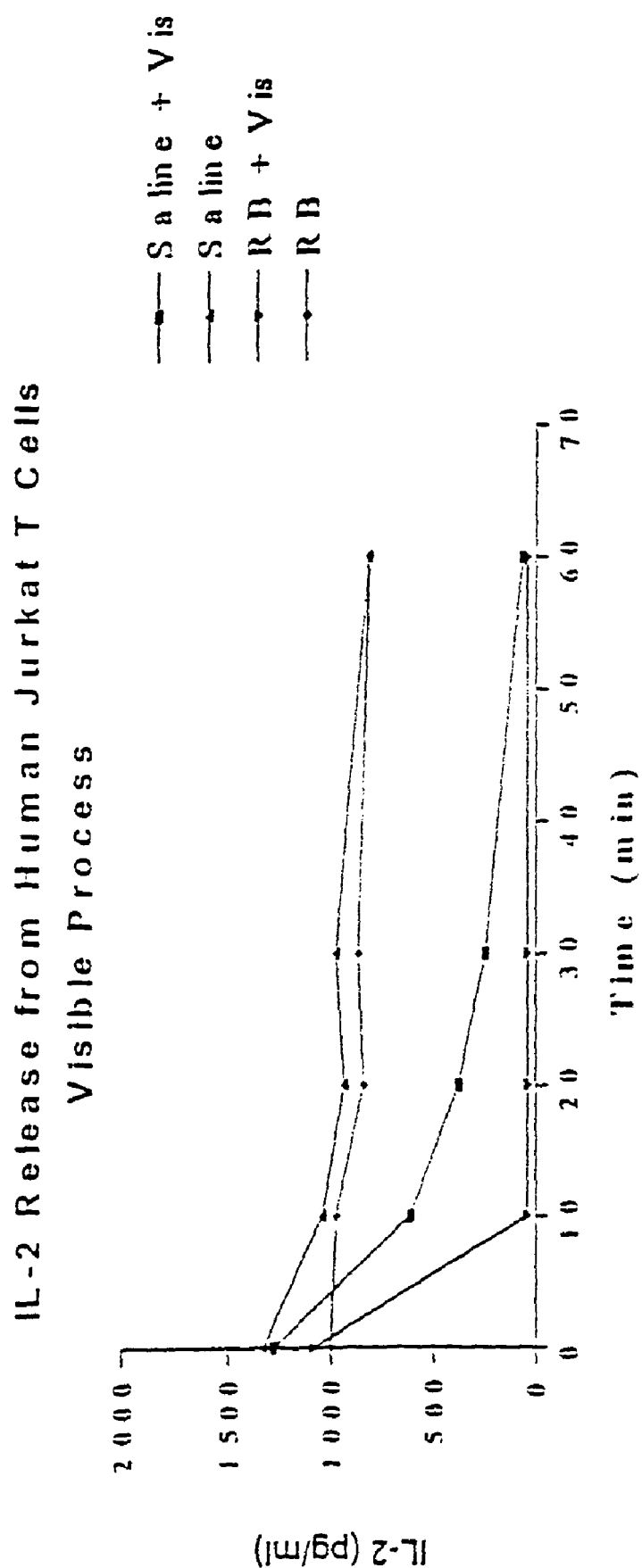
FIG. 2 is a graph showing the production of IL-2 from Jurkat cells after treatment with riboflavin and visible light.

FIGS. 1 and 2 show release of IL-2 over time by Jurkat cells after stimulation with PMA and PHA. Jurkat cells were treated with riboflavin (designated Rb in these Figs.) and either UV (ultraviolet) (see FIG. 1) or visible light (see FIG. 2) and then stimulated to produce IL-2. The addition of saline alone (no riboflavin, no light) or riboflavin alone (no light) serves as the experimental controls. Production of IL-2 by Jurkat cells upon stimulation with PMA and PHA is a measure of T-cell viability. After treating the cells with riboflavin and light, PMA and PHA are added to induce production of IL-2 and the cells are incubated overnight. IL-2 in the supernatent is detected using an ELISA assay.

FIG. 1 shows IL-2 release from Jurkat cells after exposure to riboflavin and UV light. Although difficult to see due to the substantially similar results, UV alone, as well as riboflavin in combination with UV light cause losses in cell viability and subsequent decrease in IL-2 release.

FIG. 2 shows IL-2 release from Jurkat cells after exposure to riboflavin and visible light. As can be seen from FIG. 2b, cells treated with riboflavin and visible light cause substantial losses in cell viability and subsequent decrease in IL-2 release. Visible light alone also causes a decrease in the amount of cell viability and subsequent release of IL-2, but not to the same extent as the combination of riboflavin and visible light.

Example 2

Figure 3A:
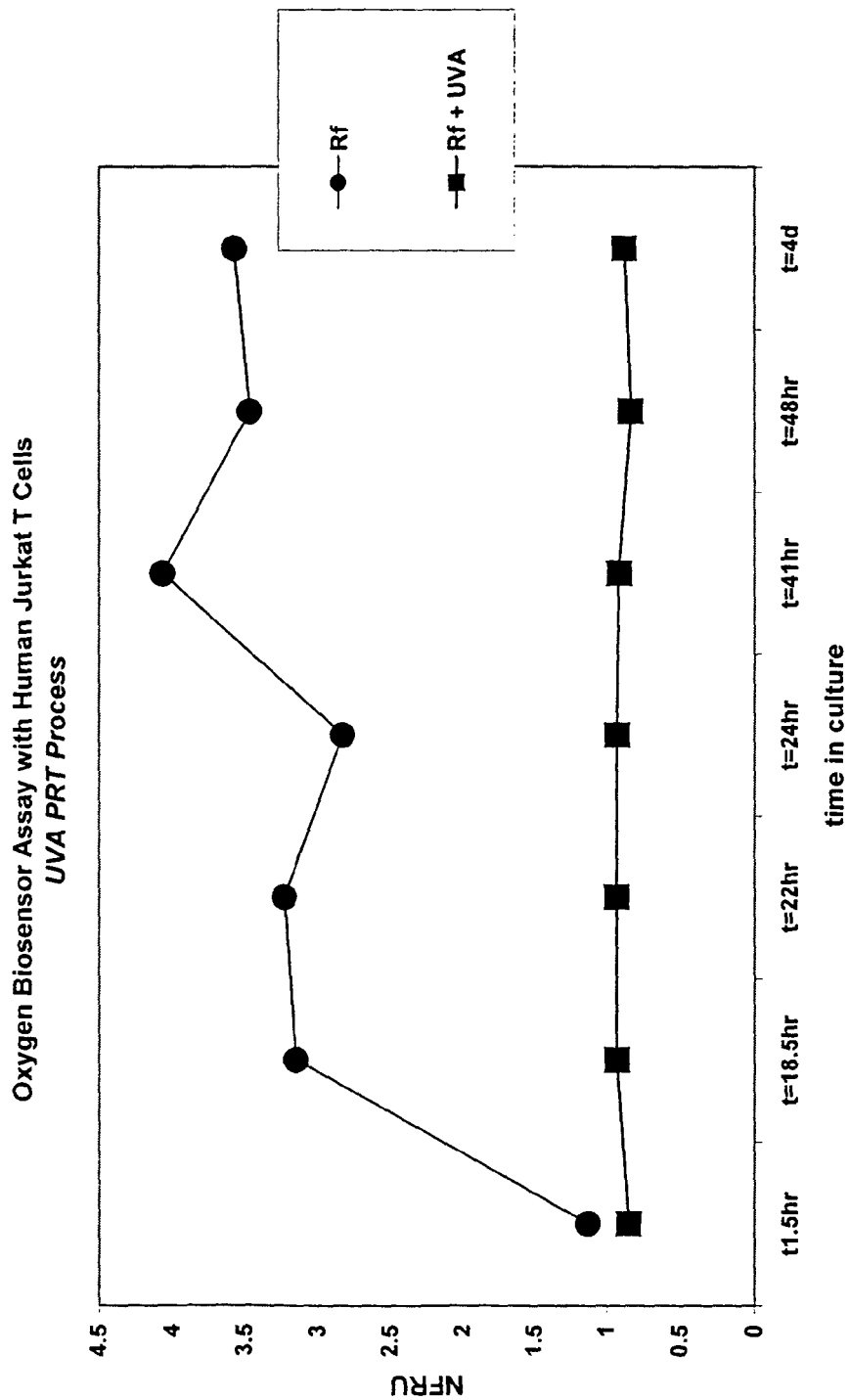
FIG. 3a is a graph showing oxygen consumption of Jurkat cells after treatment with riboflavin and UV light.
Figure 3B:
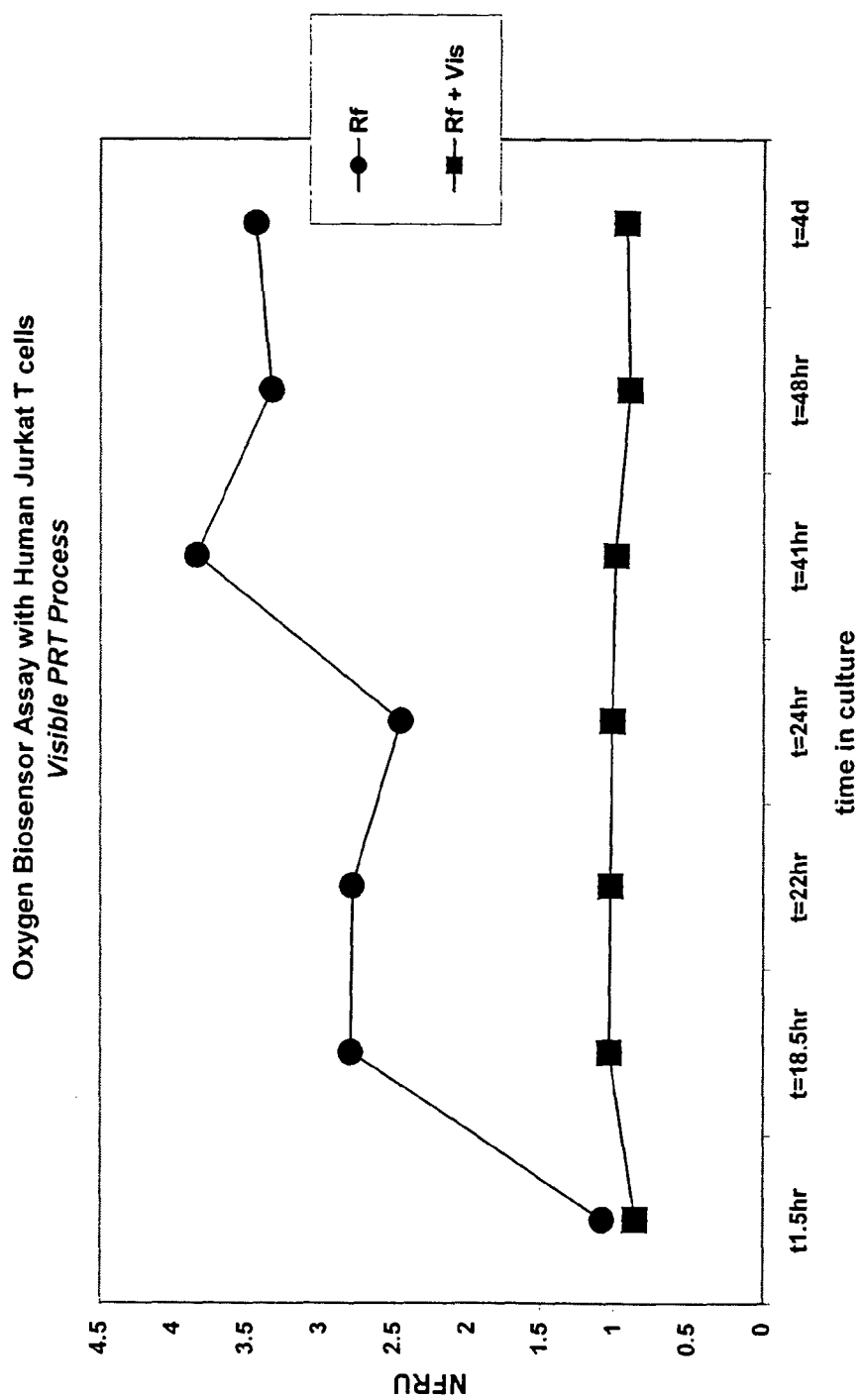
FIG. 3b is a graph showing oxygen consumption of Jurkat cells after treatment with riboflavin and visible light.

FIGS. 3a and 3b are graphs showing oxygen consumption of treated and control Jurkat cells. Oxygen consumption is a measure of cell viability. Healthy cells respire and consume oxygen, unhealthy and/or dead cells do not. A BD oxygen biosensor system was used to monitor Jurkat cell metabolism for a period of 4 days after treatment. Oxygen diffuses into the cell media from the atmosphere. The presence of oxygen quenches a fluorescent marker located at the bottom of the wells where the cells are grown. The amount of oxygen consumed by the cells is measured by the amount of fluorescence being produced. Where oxygen is used by healthy cells for respiration, fluorescence is produced.

FIG. 3a is a graph measuring the amount of fluorescence (NFRU) generated over time in Jurkat cells treated with riboflavin (designated Rf in these Figs.) and UV light. Cells which have been treated with riboflavin and UV light are damaged by the process. Consequently, the cells are not metabolically active and therefore consume no oxygen, thus producing little to no fluorescence.

FIG. 3b is a graph measuring fluoresce (NFRU) generated over time in Jurkat cells treated with riboflavin and visible light. Cells treated with riboflavin and visible light are damaged by the process. As shown in FIG. 3b, treated cells are not metabolically active and do not consume oxygen over a four day period. Little to no fluorescence is produced.

Example 3

FIG. 4 shows fragmentation of DNA of Jurkat cells over a two day period following treatment with riboflavin and either visible or ultraviolet light. Strand breaks in the DNA of Jurkat cells were measured by flow cytometry after treatment with riboflavin (designated Rf in this Fig.) and light. % positive signifies positive DNA damage. As seen in the table, on day one, UV light alone causes DNA damage in 85.5% of cells. On day 2 however, only 0.4% of the cells exposed to UV light alone displayed DNA damage. As shown in FIG. 4, exposure of the cells to UV light alone does not maintain DNA damage over time. One hypothesis is that the cells exposed to UV light alone may repair the damage. Another hypothesis is that UV alone may not prevent the growth of new healthy cells.

Upon treatment with riboflavin and UV light however, 36.1% of the DNA in the treated cells were damaged, while on day 2, 87.5% of the treated cells manifested DNA damage. The addition of riboflavin appears to maintain the damage to DNA caused by exposure to UV light.

Visible light alone did not cause DNA damage, however with the addition of riboflavin, FIG. 4 illustrates that DNA was damaged and the damage was substantially maintained over a two day period.

From the data presented above, the addition of riboflavin or other endogenous alloxazine derivatives appears to maintain the damage to white blood cell DNA.

From FIG. 4 it can be seen that the addition of riboflavin in combination with exposure to either visible or UV light not only causes fragmentation of Jurkat DNA, but maintains the damage over time.

Figure 5:
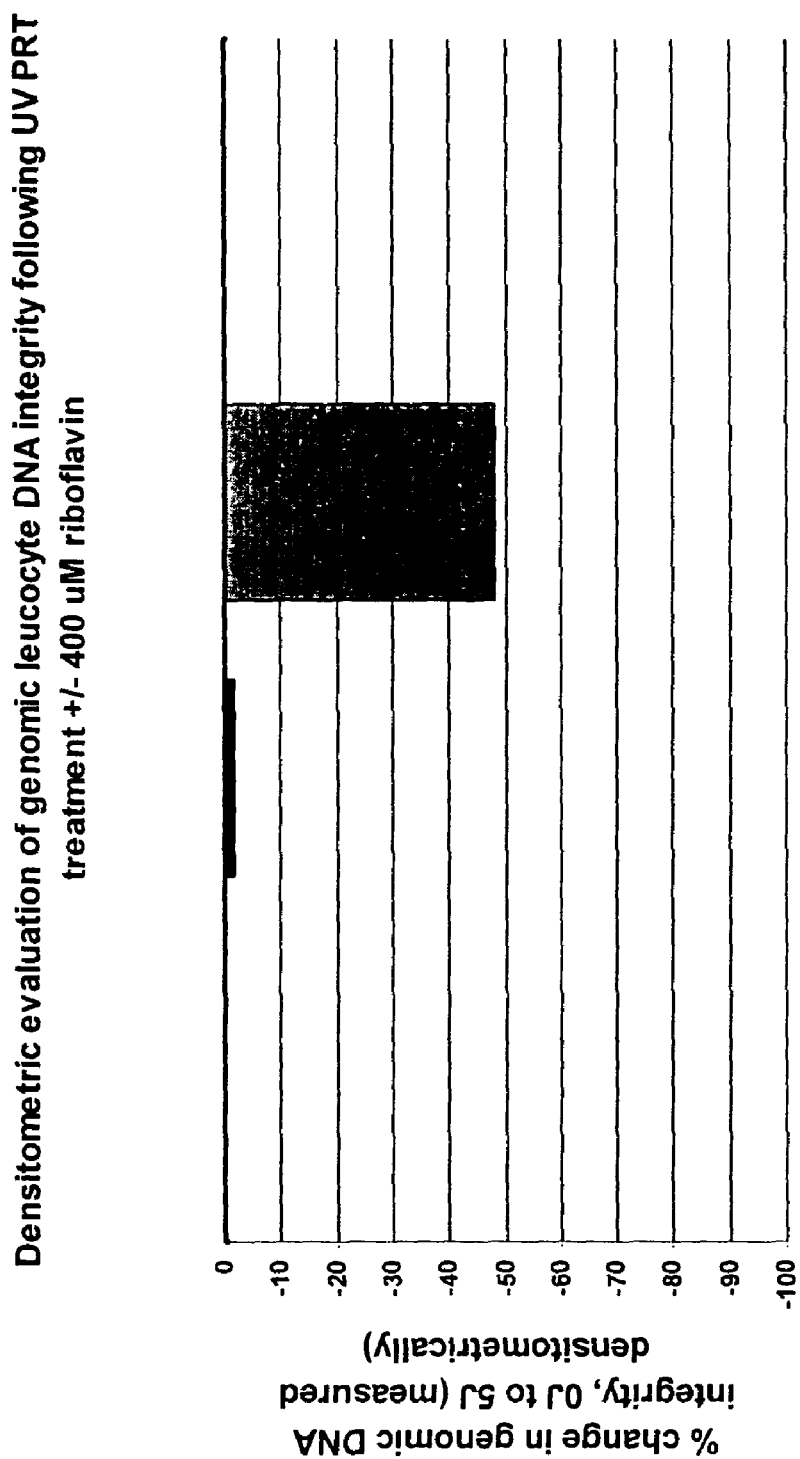
FIG. 5 is a graph measuring the percent change in the integrity of the genomic DNA of separated human leukocytes following treatment with ultraviolet light and with and without riboflavin.

FIG. 5 is a graph showing the percentage of DNA fragmentation of human leukocyte genomic DNA on an agarose gel. $3.8 \times 10^5$ autologous cells/mL in 90% plasma were added to a 1 L ELP bag. Riboflavin at a final concentration of 400 µM was added and the cells were irradiated at 320 nm at a total intensity of 5 J/cm$^2$. As can be seen from this graph, the DNA of autologous white blood cells showed around a 50% change in integrity after being exposed to riboflavin and light as compared to cells exposed to light alone. This result corresponds to the results obtained with Jurkat cells.

Example 4

To measure the effect of riboflavin and light on bacterial DNA kill, E. coli was spiked into 90% plasma. Riboflavin at a final concentration of 50 µM was added and the mixture was exposed to light at an intensity range of 0 J/cm$^2$, 10 J/cm$^2$, 17 J/cm$^2$ and 20 J/cm$^2$. After light exposure, the bacterial genomic DNA was purified using standard DNA purification techniques, and the DNA fragmentation was analyzed by standard agarose gel electrophoresis and fragmentation of the DNA was quantified using standard imaging techniques.

Figure 6A:
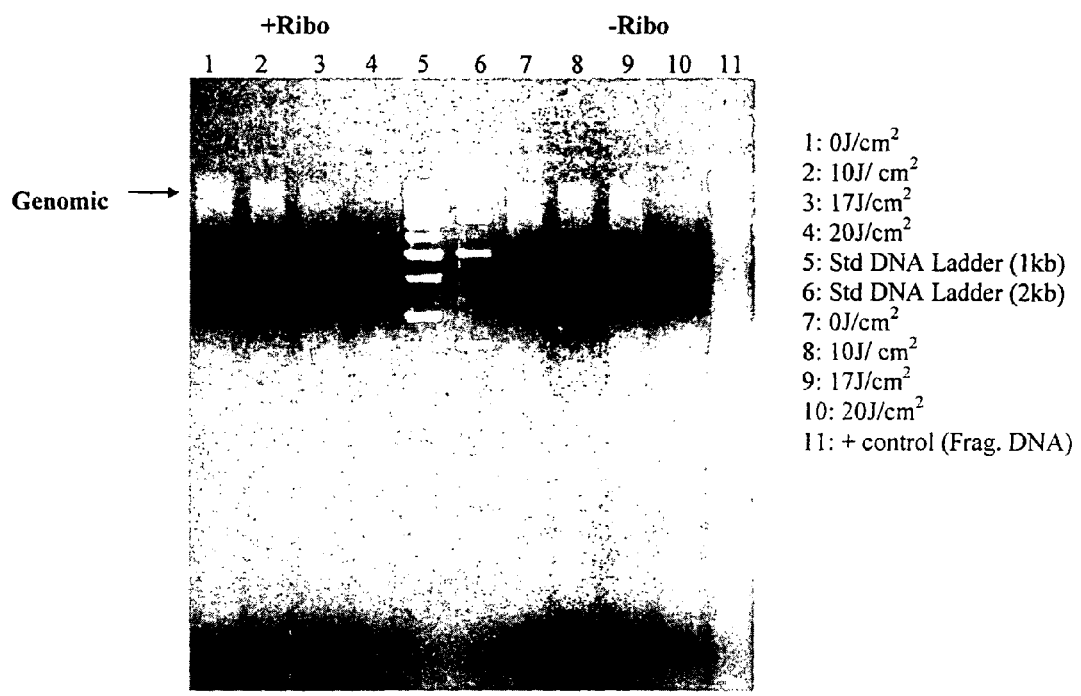
FIG. 6a is an agarose gel showing laddering of DNA after treatment with and without ultraviolet light and riboflavin.
Figure 6B:
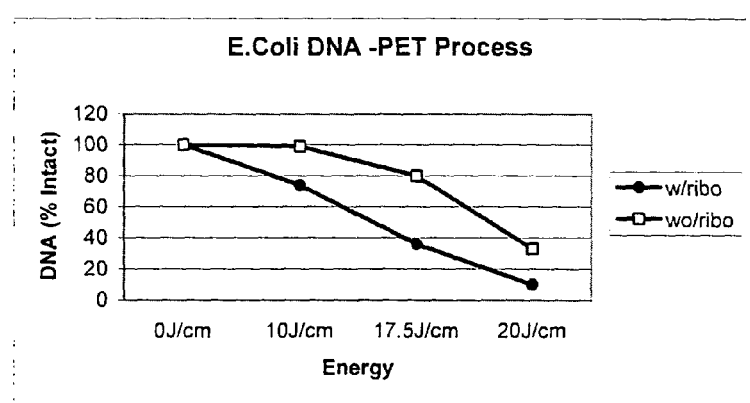

FIG. 6b is a graph showing the percentage of fragmentation of DNA (measured in terms of the percentage of DNA intact after treatment) of E. coli after exposure to UV light either with or without riboflavin. As can be seen in both the gel (see FIG. 6a) and the graph, (see FIG. 6b) the combination of riboflavin and UV light induced much greater bacterial DNA fragmentation than that induced by UV light alone. More DNA degradation occurs at lower energies with riboflavin than without.

Example 5

This study was done to determine if riboflavin and 320 nm broadband UVB light causes irreparable damage to the DNA of viruses.

It is known that UV light causes nucleic acid damage to cells. However, exposure to UV light also causes up regulation of cellular repair mechanisms. In the literature it has been reported that viruses inactivated with UV light alone will reactivate a small percentage of the time due to concurrent up regulation of the host cell's nucleic acid repair mechanisms.

To test if riboflavin and light has the same inactivating effect on the nucleic acid of viruses as it does on white blood cells and bacteria, E. coli was chosen as the host cell for lambda-phage virus. E. coli was irradiated with UV light to initially up regulate the host cells nucleic acid repair mechanisms. In this experiment, if the nucleic acid repair mechanisms of the host cell are up regulated upon initial exposure to UV light, any viral reactivation effect should be amplified. Any prevention of viral reactivation should be easily quantified.

After initial exposure to UV light, host E. coli was placed into Luria Broth growth media for 1-2 hours. Meanwhile, the lambda phage virus was irradiated with 320 nm UVB light at an intensity of 0.08 J/cm$^2$ in PBS and riboflavin at final concentrations of between 0-300 µM until a two log viral kill was achieved. The irradiated virus was then incubated with either irradiated or non-irradiated E. coli host cells for 20 minutes to allow for viral absorption. The virus infected E. coli samples were plated and allowed to grow overnight. At this time the plaques were counted to determine the number of infectious particles.

Figure 7:
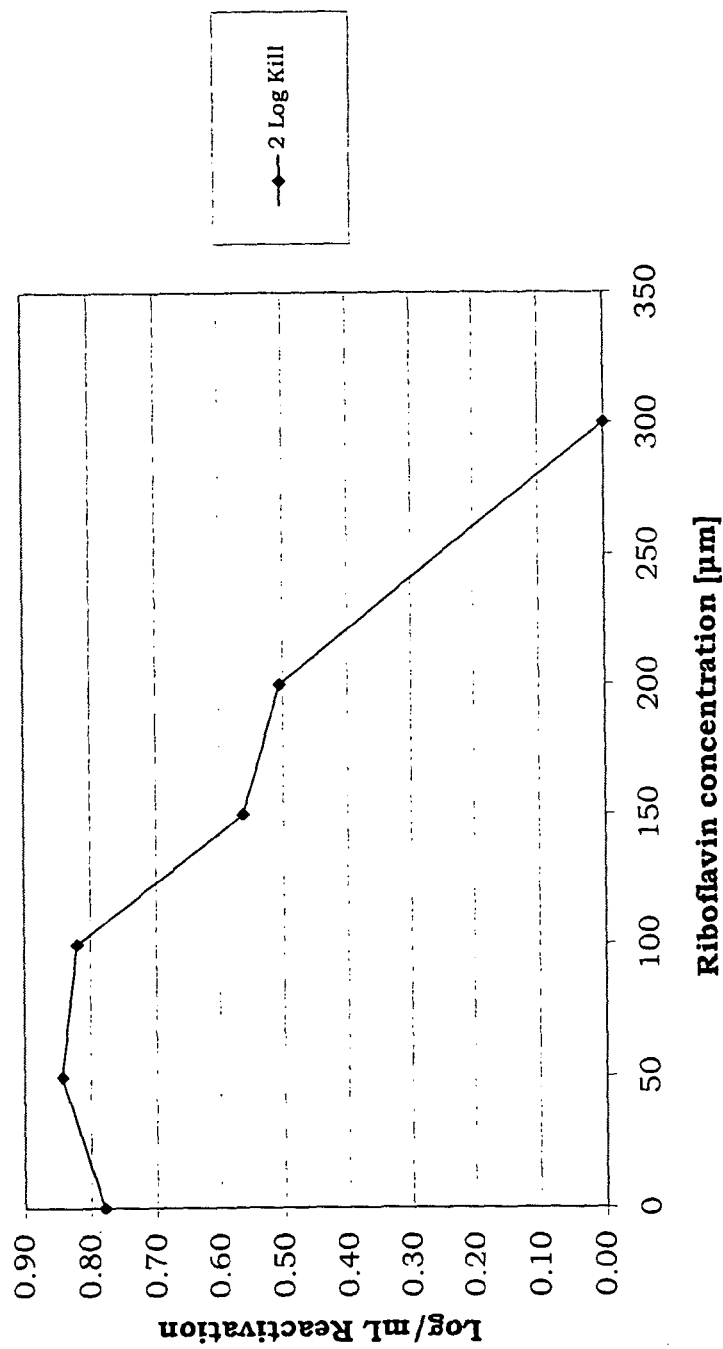
FIG. 7 shows the log reactivation of lambda-phage virus after treatment with riboflavin and ultraviolet light.

FIG. 7 shows the amount of log virus reactivation at increasing concentrations of riboflavin. The effect of riboflavin on preventing virus reactivation was dose dependant. Approximately 0.8 log virus reactivation occurred over a concentration of 0-100 µM riboflavin. At riboflavin concentrations greater than 100 µM, reactivation was progressively prevented with no reactivation occurring at 300 µM.

These results suggest that irradiation of virus with both riboflavin and light prevents reactivation of viral DNA.

The invention claimed is:

1. A process for inactivating white blood cells which may be contained in a fluid comprising:
   (a) adding riboflavin at concentration between 50-500 µM to the fluid containing white blood cells; and
   (b) exposing the fluid of step (a) to light in the UVB range to activate the riboflavin and cause damage to the nucleic acid of the white blood cells thereby substantially maintaining the damage to the nucleic acids of the white blood cells, wherein the inactivated white blood cells of step (b) are unable to reactivate upon storage or infusion into a patient.

2. The process of claim 1 wherein the fluid further comprises red blood cells.

3. The process of claim 1 wherein the fluid further comprises platelets.

4. The process of claim 1 wherein the fluid further comprises plasma.

5. A process for providing pathogen-reduced blood or blood components comprising:
   (a) damaging the nucleic acid of any pathogenic white blood cells which may be present with the blood or blood components by adding riboflavin at a concentration between 50-500 µM to the blood or blood components; and (b) exposing the blood or blood components of step (a) to light in the UVB range or visible light to activate the riboflavin to fragment the nucleic acid of the pathogenic white blood cells, wherein the pathogenic white blood cells of step (b) are unable to reactivate upon storage or infusion into a patient.

6. A fluid suitable for transfusing into a patient comprising red blood cells treated by the process of claim 1.

7. A fluid suitable for transfusing into a patient comprising platelets treated by the process of claim 1.

8. A fluid suitable for transfusing into a patient comprising plasma treated by the process of claim 1.

* * * * *